(12) United States Patent
Eppinger et al.

(10) Patent No.: US 10,996,206 B2
(45) Date of Patent: May 4, 2021

(54) METHOD FOR OBTAINING A POLLUTION CONDITION OF AT LEAST ONE COMPONENT OF A GARDENING AND/OR FORESTRY APPARATUS AND GARDENING AND/OR FORESTRY APPARATUS SYSTEM

(71) Applicant: Andreas Stihl AG & Co. KG, Waiblingen (DE)

(72) Inventors: Andreas Eppinger, Stuttgart (DE); Benjamin Frey, Berglen (DE); Friedrich Hollmeier, Rudersberg (DE); Antonio Kraemer Fernandez, Stuttgart (DE); Michael Reinert, Rudersberg (DE)

(73) Assignee: Andreas Stihl AG & Co. KG, Waiblingen (DE)

( * ) Notice: Subject to any disclaimer, the term of this patent is extended or adjusted under 35 U.S.C. 154(b) by 314 days.

(21) Appl. No.: 16/026,672

(22) Filed: Jul. 3, 2018

(65) Prior Publication Data
US 2019/0011418 A1  Jan. 10, 2019

(30) Foreign Application Priority Data
Jul. 4, 2017 (EP) .................................. 17179675

(51) Int. Cl.
| | |
|---|---|
| G01N 33/00 | (2006.01) |
| A01G 3/08 | (2006.01) |
| A01G 20/47 | (2018.01) |
| A01G 3/00 | (2006.01) |
| B27B 17/00 | (2006.01) |

(52) U.S. Cl.
CPC .......... *G01N 33/0062* (2013.01); *A01G 3/00* (2013.01); *A01G 3/085* (2013.01); *A01G 20/47* (2018.02); *B27B 17/00* (2013.01); *G01N 2033/0068* (2013.01)

(58) Field of Classification Search
CPC ............................. G01N 33/0062; B27B 17/00
USPC ........................................................ 73/31.02
See application file for complete search history.

(56) References Cited

U.S. PATENT DOCUMENTS

| | | | |
|---|---|---|---|
| 2015/0136433 A1 | 5/2015 | Nitsche et al. | |
| 2016/0342142 A1 | 11/2016 | Boeck et al. | |
| 2017/0008159 A1* | 1/2017 | Boeck | G05B 19/00 |
| 2017/0173749 A1* | 6/2017 | Stock | G08B 21/02 |
| 2017/0226808 A1* | 8/2017 | Vandapel | E21B 12/06 |

FOREIGN PATENT DOCUMENTS

| | | |
|---|---|---|
| DE | 3521348 A1 | 12/1986 |
| DE | 10 2012 208 913 A1 | 11/2013 |
| DE | 10 2012 112 833 A1 | 6/2014 |
| DE | 10 2012 224 429 A1 | 7/2014 |
| DE | 10 2014 208 980 A1 | 7/2015 |

(Continued)

*Primary Examiner* — Tarun Sinha
(74) *Attorney, Agent, or Firm* — Crowell & Moring LLP

(57) ABSTRACT

A method obtains a pollution condition of at least one component of a gardening and/or forestry apparatus. The method includes the steps of: obtaining at least one pollution parameter which describes at least one source of pollution prevalent during an operation of the gardening and/or forestry apparatus; obtaining the pollution condition of the component based on the obtained pollution parameter; and outputting and/or transmitting information based on the obtained pollution condition.

15 Claims, 1 Drawing Sheet

(56) References Cited

FOREIGN PATENT DOCUMENTS

| | | |
|---|---|---|
| DE | 10 2014 209 032 A1 | 7/2015 |
| DE | 10 2015 226 796 A1 | 12/2016 |
| DE | 10 2015 217 053 A1 | 3/2017 |
| DE | 10 2015 217 825 A1 | 3/2017 |
| WO | WO 2015/110245 A1 | 7/2015 |

* cited by examiner

METHOD FOR OBTAINING A POLLUTION CONDITION OF AT LEAST ONE COMPONENT OF A GARDENING AND/OR FORESTRY APPARATUS AND GARDENING AND/OR FORESTRY APPARATUS SYSTEM

CROSS REFERENCE TO RELATED APPLICATION

This application claims priority under 35 U.S.C. § 119 from European Patent Application No. 17179675.8, filed Jul. 4, 2017, the entire disclosure of which is herein expressly incorporated by reference.

BACKGROUND AND SUMMARY OF THE INVENTION

The invention relates to a method for obtaining a pollution condition of at least one component of a gardening and/or forestry apparatus and to a gardening and/or forestry apparatus system.

A method for obtaining a pollution condition of at least one component of a gardening and/or forestry apparatus and a gardening and/or forestry apparatus system are known.

The invention is based on the problem of providing a method for obtaining a pollution condition of at least one component of a gardening and/or forestry apparatus, which method exhibits improved properties, in particular more functions. The invention is furthermore based on the problem of providing a gardening and/or forestry apparatus system.

The invention solves this problem by providing a method and a gardening and/or forestry apparatus system for obtaining a pollution condition of at least one component of a gardening and/or forestry apparatus in accordance with claimed embodiments of the invention. Advantageous developments and/or configurations of the invention are described and claimed herein.

The method according to the invention, in particular an automatic method, for obtaining a pollution condition or pollution degree, in particular an assumed real or expected pollution condition or pollution degree, of at least one component of a gardening and/or forestry apparatus has the steps of: a) obtaining, in particular automatically obtaining, at least one pollution parameter which describes at least one source of pollution prevalent during an operation of the gardening and/or forestry apparatus; b) obtaining, in particular automatically obtaining, the pollution condition of the component based on the obtained pollution parameter; c) outputting, in particular automatically outputting, and/or transmitting, in particular automatically transmitting, information based on the obtained pollution condition.

The method makes it possible to indirectly obtain the pollution condition of the component. In other words, the pollution condition of the component does not need to be obtained in a direct manner. This can make it possible to obtain or predict the pollution condition of the component even before the operation of the gardening and/or forestry apparatus, in particular if the at least one source of pollution prevalent during the operation of the gardening and/or forestry apparatus can already be known or obtained, in particular predicted, before the operation.

In addition or alternatively, the method makes it possible owing to the information to take care of the component, in particular before it can be too strongly polluted. In particular it is possible, if the need arises, for in particular a gardening and/or forestry worker or a user of the gardening and/or forestry apparatus to procure in time and/or to carry along cleaning and/or maintenance material and/or a replacement component. The method consequently makes it possible to protect the gardening and/or forestry apparatus, or the component thereof, against poor performance and/or damage due to excessive pollution of the component.

In particular, the information can be output optically, acoustically and/or haptically. The optical output can include a display. The optical output can include superposition or projection of the information into a field of view of the gardening and/or forestry worker. In addition or alternatively, the information can be transmitted to a database and/or a network and/or a hub and/or a cloud and/or similar, in particular to the Internet.

The gardening and/or forestry apparatus can take the form of a hand-guided gardening and/or forestry apparatus, in particular a hand-held gardening and/or forestry apparatus or a ground-guided gardening and/or forestry apparatus. Hand-guided, in particular hand-held, gardening and/or forestry apparatus can mean that the gardening and/or forestry apparatus can have a maximum mass of 50 kilograms (kg), in particular of 20 kg, in particular of 10 kg.

The pollution parameter can include or be a value and/or an amount. The pollution condition can include or be a value and/or an amount.

The step b) can be executed at the same time as step a) and/or after the said step a). The step c) can be executed at the same time as step b) and/or after the said step b).

In one development of the invention, the step a) includes: obtaining or capturing the pollution parameter using at least one sensor which is provided separate from the component, in particular from the gardening and/or forestry apparatus. In other words, the sensor cannot, or need not, be a constituent part of the component, in particular not a constituent part of the gardening and/or forestry apparatus. In particular, the sensor can be configured to capture or measure the source of pollution directly. In other words, the sensor cannot or need not be configured to measure, in particular gauge, the component.

In a development of the invention, the pollution condition of the component depends on the operation of the gardening and/or forestry apparatus. The component is exposed to the source of pollution during the operation of the gardening and/or forestry apparatus. The method comprises the step of: obtaining, in particular automatically obtaining, data of the operation of the gardening and/or forestry apparatus. Step b) comprises: obtaining the pollution condition of the component based on the obtained data of the operation. This makes possible relatively accurate obtaining of the pollution condition. Step b) can be performed at the same time as or, temporally, after the obtaining of the data of the operation.

In one embodiment of the invention, the data of the operation include a running time of the gardening and/or forestry apparatus, in particular a rotation speed curve, in particular over the running time, of the gardening and/or forestry apparatus. The running time can be obtained in particular by capturing a sound produced by the operation of the gardening and/or forestry apparatus, in particular using the above-described sensor. The sensor can include a sound converter, in particular a microphone. The running time and in particular the rotation speed curve can depend on, or at least be influenced by, a working method with the gardening and/or forestry apparatus. Accordingly, the pollution condition can depend on, or at least be influenced by, the working method. The running time can include or be a value and/or an amount, in particular in seconds, minutes, hours, days and/or a greater unit of time. The rotation speed curve can have or be a value or a value set and/or an amount, in particular in the unit revolutions per minute.

In a development of the invention, the component has a cylinder, a fan propeller, an air filter grille, an air filter and/or a cooling fin, or is such a specific component. Typically, a component which is developed in this way can interact with ambient air of the gardening and/or forestry apparatus, in particular for the combustion of the ambient air and/or for cooling with the ambient air. Excessive pollution of such a component can result in an insufficient supply of combustion air and/or insufficient cooling. In particular, the source of pollution can be included in the ambient air. The interaction with the ambient air can consequently lead to the pollution.

In a development of the invention, the gardening and/or forestry apparatus includes a saw, a pole pruner, a clearing saw or a brush cutter, a blower device and/or a leaf blower, or is such a specific gardening and/or forestry apparatus. Typically, a thus developed gardening and/or forestry apparatus during operation thereof, or the component thereof, can be exposed to the source of the pollution or even cause the latter. In particular, the saw, the pole pruner, the clearing saw or the brush cutter, the blower device or the leaf blower can each be referred to as a hand-held gardening and/or forestry apparatus.

In a development of the invention, the source of pollution includes dust and/or tree resin and/or pollen, or is such a specific source of pollution. The pollution parameter includes a dust concentration and/or an amount of resin and/or a pollen concentration, or is such a specific pollution parameter. The dust concentration can include or be a value and/or an amount. The amount of resin can include or be a value and/or an amount. The pollen concentration can include or be a value and/or an amount. In particular, such a source of pollution can be caused by the operation of the gardening and/or forestry apparatus itself. The dust can include silicate. The amount of resin can depend on, or at least be influenced by, a resin component in wood. The above-described sensor can be configured to obtain the dust concentration and/or the amount of resin and/or the pollen concentration and/or to obtain a transmission, in particular of the ambient air, which can depend on, or at least be influenced by, the dust and/or the tree resin and/or the pollen, or their extent or degree. The sensor can include a transmission determination means.

In one development of the invention, the step a) includes: receiving, in particular receiving in a cable-free or wire-free manner, or calling up the pollution parameter, in particular from a database and/or a network, in particular using a receiver unit.

In one development of the invention, the step a) includes: obtaining, in particular capturing and/or receiving, a meteorological parameter and obtaining the pollution parameter as a function of or based on the obtained meteorological parameter. In particular, the meteorological parameter can include an air temperature, an air humidity, a dew point, an air pressure, an air density, an air composition, a wind direction, a wind speed, a type of precipitation, an amount of precipitation and/or a season. In particular the air temperature and/or the humidity and/or the dew point and/or the air pressure and/or the air density and/or the air composition and/or the wind direction and/or the wind speed and/or the type of precipitation and/or the amount of precipitation can depend on, or at least be influenced by, the season. The meteorological parameter can include or be a value and/or an amount. The source of pollution, or the extent or degree thereof, can depend on, or at least be influenced by, the meteorological parameter. In particular, wind can transport the source of pollution to the component or away from it. In addition or alternatively, precipitation can remove the source of pollution, in particular dust, tree resin and/or pollen, where present, in particular wash them out of the ambient air. The above-described sensor can be configured to obtain the meteorological parameter. The sensor can include a thermometer, a hygrometer, a dew point mirror hygrometer, a barometer and/or a precipitation gauge.

In one development of the invention, the step a) includes: obtaining, in particular capturing and/or receiving, a material of a workpiece or object to be treated by the gardening and/or forestry apparatus and obtaining the pollution parameter as a function of or based on the obtained material. The source of pollution, or the extent or degree thereof, can in particular depend on, or at least be influenced by, the material. The workpiece can include or be a piece of wood, in particular a tree. The material can include a type of wood or a type of tree. The dust concentration and/or the amount of resin, where present, can depend on, or at least be influenced by, the type of wood or the type of tree. The above-described sensor can be configured to obtain the material. The sensor can include a camera for obtaining an image of the workpiece, in particular the surface nature thereof, and an image processing device for obtaining the material from the image.

In one development of the invention, the step a) includes: obtaining, in particular capturing or specifying, a position of the operation of the gardening and/or forestry apparatus and obtaining the pollution parameter as a function of, or based on, the obtained position. In addition or alternatively, the step a) includes: obtaining, in particular capturing and/or specifying, a marking of the workpiece or object to be treated by the gardening and/or forestry apparatus and obtaining the pollution parameter as a function of, or based on, the obtained marking. From the obtained position, in particular the pollution parameter for this position and/or the meteorological parameter for this position and/or the material for this position can be obtained, in particular received. From the obtained marking, the position for this marking and/or for this workpiece can be obtained and thus the pollution parameter can be obtained, as previously described. In addition or alternatively, the material of the workpiece and consequently the pollution parameter can be obtained from the obtained marking. The above-described sensor can be configured to obtain the position and/or the marking. The sensor can have a position determination sensor, in particular a satellite position determination receiver. In addition or alternatively, the sensor may include a reader for reading the marking, in particular a camera and an image processing device. In particular, the marking can be made on the workpiece, in particular by the gardening and/or forestry worker. The marking can include at least one symbol, in particular a letter and/or a number, and/or a code, in particular a bar code and/or a QR code. In addition or alternatively, the marking can have or be an NFC chip.

In a development of the invention, the information includes the obtained pollution condition, or is the obtained pollution condition. In addition or alternatively, the method includes the step: obtaining, in particular automatically obtaining, a cleaning and/or maintenance reminder for the component based on the obtained pollution condition. The information includes the cleaning and/or maintenance reminder, or is the cleaning and/or maintenance reminder. This makes possible professional cleaning and/or maintenance of the component. In particular, the cleaning and/or maintenance reminder can indicate that a cleaner spray, which can include in particular a resin-detaching substance, can be or should be injected.

Furthermore, the invention relates to a gardening and/or forestry apparatus system which can be configured in particular for performing the above-described method. The gardening and/or forestry apparatus system according to the invention includes a pollution parameter determination device, a pollution condition determination device and an output and/or transmission device. The pollution parameter determination device is configured to obtain at least one pollution parameter which describes the at least one source of pollution prevalent during the operation of the gardening and/or forestry apparatus. The pollution condition determination device is configured to obtain the pollution condition of the at least one component of the gardening and/or forestry apparatus based on the obtained pollution parameter. The output and/or transmission device is configured to output and/or to transmit information based on the obtained pollution condition.

The gardening and/or forestry apparatus system can allow the same advantages as the above-described method.

In particular, the pollution parameter determination device can include a receiver unit. The receiver unit can include a UMTS, WLAN and/or Bluetooth receiver unit, or a receiver unit based on another technology. In addition or alternatively, the pollution parameter determination device can include the above-described sensor. The pollution condition determination device can include a computation and/or memory unit. The output and/or transmission device can include a display, a sound converter and/or a vibration device. The display can in particular be configured to display the information in the field of view of the gardening and/or forestry worker and/or to project or superimpose it therein. The display can be called a head-up display. This can be called virtual reality and/or augmented reality. In particular, the display can be configured to be arranged in the region or even on the head of the gardening and/or forestry worker. The display can be called a head-mounted display. In addition or alternatively, the output and/or transmission device can include a transmitter unit. The transmitter unit can include a UMTS, WLAN and/or Bluetooth transmitter unit, or a transmitter unit based on another technology.

In a development of the invention, the gardening and/or forestry apparatus system has a mobile or portable, in particular hand-held, determination device. The mobile determination device includes the pollution parameter determination device, the pollution condition determination device and/or the output and/or transmission device. The mobile determination device makes it possible for it to be carried along in a user-friendly manner. In particular, the mobile determination device can include a smart phone and/or a smart watch. The mobile determination device can be provided separate from the component, in particular from the gardening and/or forestry apparatus.

In a development, the gardening and/or forestry apparatus system includes the gardening and/or forestry apparatus.

Other objects, advantages and novel features of the present invention will become apparent from the following detailed description of one or more preferred embodiments when considered in conjunction with the accompanying drawings.

DETAILED DESCRIPTION OF THE DRAWINGS

Figure 2:
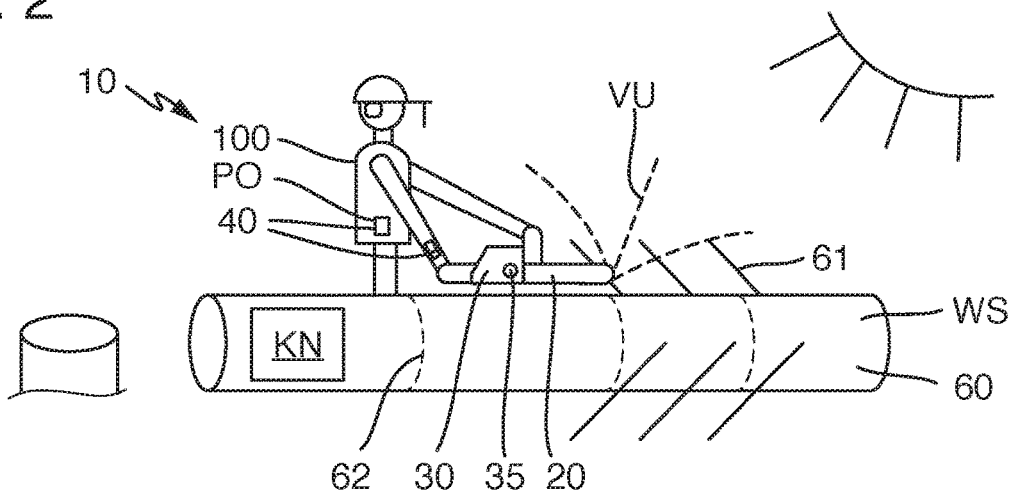
FIG. 2 is a perspective view of a gardening and/or forestry apparatus system according to an embodiment of the invention having at least one mobile determination device and having a gardening and/or forestry apparatus during a treatment of a workpiece.
Figure 3:
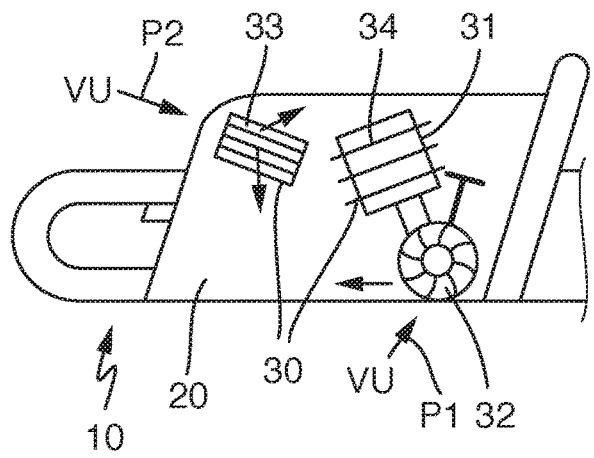
FIG. 3 is a view of a longitudinal section of the gardening and/or forestry apparatus of FIG. 2.
Figure 4:
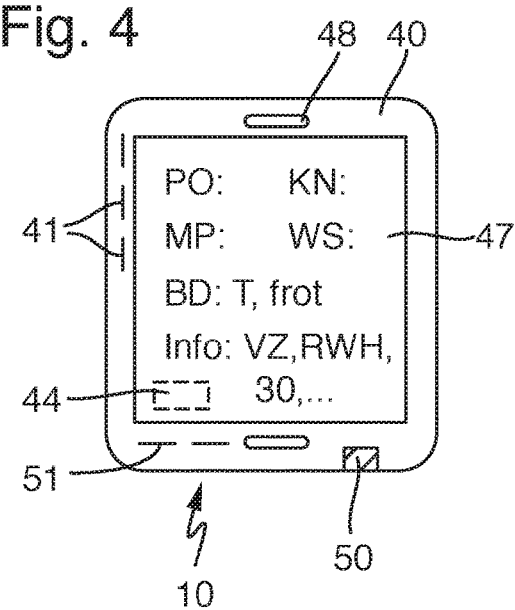
FIG. 4 is a front view of the mobile determination device of FIG. 2.

FIGS. 2 to 4 show a gardening and/or forestry apparatus system 10 according to the invention. The gardening and/or forestry apparatus system 10 includes a pollution parameter determination device 41, 50, 51, a pollution condition determination device 44 and an output and/or transmission device 41, 47, 48. The pollution parameter determination device 41, 50, 51 is configured to obtain at least one pollution parameter SP, or the value thereof. The pollution parameter SP describes at least one source of pollution VU prevalent during an operation of an, in particular hand-held, gardening and/or forestry apparatus 20. The pollution condition determination device 44 is configured to obtain a pollution condition VZ, or the value thereof, of at least one component 30 of the gardening and/or forestry apparatus 20 based on the obtained pollution parameter SP. The output and/or transmission device 41, 47, 48 is configured to output and/or to transmit information Info based on the obtained pollution condition VZ.

The gardening and/or forestry apparatus system 10 furthermore includes at least one mobile determination device 40. The mobile determination device 40 includes the pollution parameter determination device 41, 50, 51, the pollution condition determination device 44 and the output and/or transmission device 41, 47, 48. In alternative exemplary embodiments, it may suffice if the mobile determination device can include either the pollution parameter determination device or the pollution condition determination device or the output and/or transmission device. In the exemplary embodiment shown, the gardening and/or forestry apparatus system 10 includes two mobile determination devices 40. One mobile determination device 40 includes a smartphone, which is situated in FIG. 2 in a pocket of a gardening and/or forestry worker 100. The other mobile determination device 40 includes a smartwatch, which is situated in FIG. 2 on the right arm of the gardening and/or forestry worker 100. In alternative exemplary embodiments, it may suffice if the mobile determination device can include either the smart phone or the smart watch.

In addition, the gardening and/or forestry apparatus system 10 includes the gardening and/or forestry apparatus 20.

Figure 1:
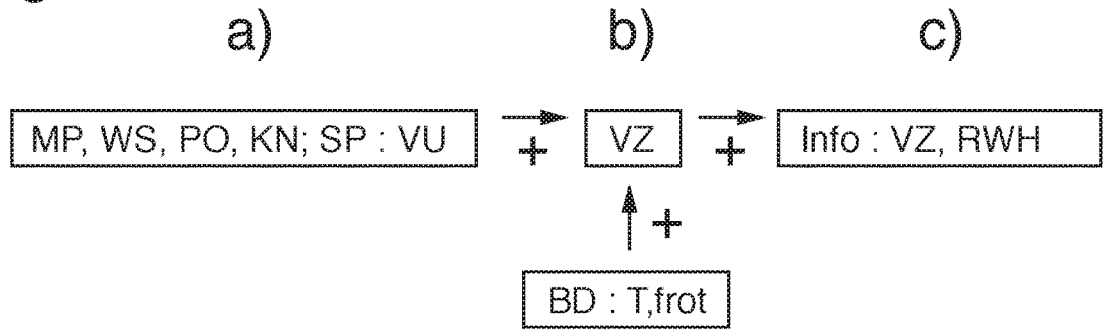
FIG. 1 is a flowchart of an exemplary method according to the invention.

FIG. 1 shows a method according to the invention for obtaining the pollution condition VZ of the at least one component 30 of the gardening and/or forestry apparatus 20, in particular using the above-described gardening and/or forestry apparatus system 10. The method includes the steps of: a) obtaining the at least one pollution parameter SP which describes the at least one source of pollution VU prevalent during the operation of the gardening and/or forestry apparatus 20; b) obtaining the pollution condition VZ of the component 30 based on the obtained pollution parameter SP; c) outputting and transmitting information Info based on the obtained pollution condition VZ. In alternative exemplary embodiments, it may suffice if the step c) can include either the outputting or the transmitting.

Specifically, the gardening and/or forestry apparatus 20 includes a saw, in particular a motor-driven chainsaw. In alternative exemplary embodiments, the gardening and/or forestry apparatus can additionally or alternatively include a pole pruner, a clearing saw or a brush cutter, a blower device and/or a leaf blower.

In FIG. 2, the forestry worker 100 uses the gardening and/or forestry apparatus 20 to treat a workpiece 60 to be treated in the form of a tree trunk which was previously felled using the gardening and/or forestry apparatus 20. Specifically, the forestry worker 100 removes branches 61. Subsequently, he will cut through the tree trunk 60 using the gardening and/or forestry apparatus 20, in particular at the places indicated by dashed lines 62. During operation, the gardening and/or forestry apparatus 20, or the component 30 thereof, was, is and will be exposed to the source of pollution VU, in particular cause said pollution at least in part itself.

In the exemplary embodiment shown, the source of pollution VU includes dust and tree resin, in particular from the tree trunk 60 and the branches 61. In alternative exemplary embodiments, the source of pollution can include either dust or tree resin. In alternative exemplary embodiments, the source of pollution can furthermore additionally or alternatively include pollen. In the exemplary embodiment shown, the pollution parameter SP includes a dust concentration and an amount of resin. In alternative exemplary embodiments, the pollution parameter can accordingly include either a dust concentration or an amount of resin. In alternative exemplary embodiments, the pollution parameter can furthermore additionally or alternatively include a pollen concentration.

Specifically, the at least one component 30 includes a cylinder 31, a fan propeller 32, an air filter grille 35, an air filter 33 and a cooling fin 34, as can be seen in FIGS. 2 and 3. The air filter grille 35 is arranged in front of the fan propeller 32. In alternative exemplary embodiments, it may suffice if the component 30 can include either the cylinder or the air propeller or the air filter grille or the air filter or the cooling fin. These components 30 interact with ambient air of the gardening and/or forestry apparatus 20, in particular for combustion of the ambient air and/or for cooling with the ambient air, as is indicated in FIG. 3 by the arrows P1, P2. Excessive pollution of such a component 30 can result in an insufficient supply of combustion air and/or insufficient cooling. In the exemplary embodiment shown, the source of pollution VU is included in the ambient air. The interaction with the ambient air consequently leads to the pollution.

Specifically, the pollution parameter determination device includes at least one sensor 50, 51, which is provided separate from the component 30. Accordingly, the step a) includes: obtaining the pollution parameter SP using the at least one sensor 50, 51.

In the exemplary embodiment shown, the sensor 50 takes the form of a microphone. Furthermore, the sensor 51 is configured as a position determination sensor, in particular as a satellite position determination receiver. In addition, the pollution parameter determination device has a camera (not illustrated), which is situated at a rear side of the mobile determination device 40, and an image processing device (not illustrated). In alternative exemplary embodiments, the pollution parameter determination device can include only part of the above-described sensors. In alternative exemplary embodiments, the pollution parameter determination device can furthermore additionally or alternatively include other sensors.

Accordingly, the step a) includes: obtaining a position PO of the operation of the gardening and/or forestry apparatus 20, in particular using the sensor 51, and obtaining the pollution parameter SP as a function of the obtained position PO.

Furthermore, the step a) includes: obtaining a marking KN of the workpiece 60 to be treated by the gardening and/or forestry apparatus 20, in particular using the camera and the image processing device, and obtaining the pollution parameter SP as a function of the obtained marking KN.

In addition, the step a) includes: obtaining a material WS of the workpiece 60 to be treated by the gardening and/or forestry apparatus 20, in particular using the camera and the image processing device, and obtaining the pollution parameter SP as a function of the obtained material WS. In the exemplary embodiment shown, the material WS includes a type of wood or a type of tree. The dust concentration and the amount of resin depend on the type of wood or the type of tree.

The pollution parameter determination device furthermore includes a receiver and transmitter unit 41. The receiver and transmitter unit 41 is configured as a radio antenna.

Accordingly, the step a) includes: receiving the pollution parameter SP, in particular from a database and/or a network, in particular using the receiver and transmitter unit 41.

Furthermore, the step a) includes: obtaining, in particular receiving, a meteorological parameter MP, in particular using the receiver and transmitter unit 41, and obtaining the pollution parameter SP as a function of the obtained meteorological parameter MP. In the exemplary embodiment shown, the meteorological parameter MP includes an air temperature, an air humidity, a dew point, an air pressure, an air density, an air composition, a wind direction, a wind speed, a type of precipitation, an amount of precipitation and a season. In alternative exemplary embodiments, it may suffice if the meteorological parameter can include only part of these specific meteorological parameters. In the situation shown in FIG. 2, the season is summer. The sun is shining and the air temperature is relatively high. There is no precipitation which could wash out in particular the source of pollution VU in the form of the dust and the tree resin from the ambient air. Consequently, the pollution parameter SP or the value thereof, in particular the dust concentration thereof and the amount of resin thereof, is relatively high. This can lead relatively quickly in terms of time to a relatively strong pollution condition VZ of the component 30. Typically, in a different season, for example in winter, with a relatively lower air temperature or with precipitation in the form of rain, the pollution parameter, or the value thereof, will be relatively lower. Typically, this will lead relatively slowly in terms of time to a relatively strong pollution condition of the component.

Specifically, from the obtained position PO, the pollution parameter SP for this position PO and/or the meteorological parameter MP for this position PO and/or the material WS for this position PO can be obtained, in particular received. From the obtained marking KN, the position PO for this marking KN and/or for the workpiece 60 to be treated can furthermore be obtained and thus the pollution parameter SP can be obtained, as previously described. In addition or alternatively, the material WS of the workpiece 60 to be treated and consequently the pollution parameter SP can be obtained from the obtained marking KN.

In alternative exemplary embodiments, it may suffice if the step a) can include: either directly obtaining or receiving the pollution parameter or obtaining the meteorological parameter or obtaining the material or obtaining the position or obtaining the marking.

In the exemplary embodiment shown, the pollution condition VZ of the component 30 depends on the operation of the gardening and/or forestry apparatus 20. The component 30 is exposed to the source of pollution VU during the operation of the gardening and/or forestry apparatus 20. The method comprises the step of: obtaining data of the operation BD of the gardening and/or forestry apparatus 20. The step b) includes: obtaining the pollution condition VZ of the component 30 based on the obtained data of the operation BD.

Specifically, the data of the operation BD include a running time T of the gardening and/or forestry apparatus 20, in particular a rotation speed curve frot of the gardening and/or forestry apparatus 20. In the exemplary embodiment shown, the running time T and the rotation speed curve frot are obtained by capturing a sound produced by the operation of the gardening and/or forestry apparatus 20, in particular using the above-described sensor 50, which takes the form of a microphone.

In the situation of the relatively high value of the pollution parameter SP shown in FIG. 2, a relatively long running time T, and in particular a relatively high rotation speed frot, of the gardening and/or forestry apparatus 20 will lead to a relatively strong pollution condition VZ of the component 30. A relatively short running time T, and in particular a relatively low rotation speed frot, of the gardening and/or forestry apparatus 20 will lead to a relatively low pollution condition VZ of the component 30. In a different situation of a relatively low value of the pollution parameter, a relatively long running time, and in particular a relatively high rotation speed, of the gardening and/or forestry apparatus will likewise lead to a relatively lower pollution condition VZ of the component. A relatively short running time, and in particular a relatively low rotation speed, of the gardening and/or forestry apparatus will lead rarely or not at all to a pollution of the component, and thus to a pollution condition equal to zero.

Specifically, the pollution condition determination device 44 includes a computation and/or memory unit. The latter obtains, on the basis of the pollution parameter SP, or the value thereof, and on the basis of the obtained data of the operation BD, the pollution condition VZ of the component 30.

Furthermore, the output and/or transmission device includes a display 47 in the form of a touchscreen, a sound generator 48 in the form of a loudspeaker and a vibration device (not illustrated). In alternative exemplary embodiments, it may be sufficient if the output and/or transmission device can either include the display or the sound generator or the vibration device.

Accordingly, the information Info is output optically, acoustically and/or haptically, in particular in time before an excessive pollution condition VZ of the component 30.

In addition, the output and/or transmission device includes the receiver and transmitter unit 41.

Accordingly, the information Info can be transmitted to a database and/or a network.

Specifically, the information Info includes the obtained pollution condition VZ, in particular broken down for each component 30, 31, 32, 33, 34, 35.

The method furthermore includes the step: obtaining a cleaning and/or maintenance reminder RWH for the component 30 based on the obtained pollution condition VZ. The information Info includes the cleaning and/or maintenance reminder RWH, in particular broken down for each component 30.

As the exemplary embodiments shown and explained above make clear, the invention provides an advantageous method for obtaining a pollution condition of at least one component of a gardening and/or forestry apparatus, which method exhibits improved properties, in particular more functions, and a gardening and/or forestry apparatus system. In particular, the method and the gardening and/or forestry apparatus system permit obtaining the pollution condition of the component in indirect fashion. The method and the gardening and/or forestry apparatus system furthermore permit, on the basis of information based on the obtained pollution condition, taking care of the component or taking precautions therefor, in particular before it can be excessively polluted.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A method for indirectly obtaining a pollution condition of at least one component of a gardening and/or forestry apparatus, the method comprising the steps of:
   a) obtaining at least one pollution parameter which describes at least one source of pollution prevalent during an operation of the gardening and/or forestry apparatus;
   b) indirectly obtaining the pollution condition of the component based on the obtained pollution parameter; and
   c) outputting and/or transmitting information based on the obtained pollution condition, wherein
   the information includes the obtained pollution condition, and/or
   the method further comprises the step of:
   obtaining a cleaning and/or maintenance reminder for the component based on the obtained pollution condition, wherein the information includes the cleaning and/or maintenance reminder.

2. The method according to claim 1, wherein
the step a) includes: obtaining the pollution parameter using at least one sensor which is provided separate from the component.

3. The method according to claim 1, wherein
the pollution condition of the component depends on the operation of the gardening and/or forestry apparatus, wherein the component is exposed to the source of pollution during the operation of the gardening and/or forestry apparatus,
the method further comprising the step of:
obtaining data of the operation of the gardening and/or forestry apparatus, and
wherein the step b) includes: obtaining the pollution condition of the component based on the obtained data of operation.

4. The method according to claim 3, wherein
the data of operation include a running time of the gardening and/or forestry apparatus.

5. The method according to claim 4, wherein
the running time of the gardening and/or forestry apparatus is a rotation speed curve of the gardening and/or forestry apparatus.

6. The method according to claim 1, wherein
the component includes a cylinder, a fan propeller, an air filter grille, an air filter and/or a cooling fin.

7. The method according to claim 1, wherein
the gardening and/or forestry apparatus includes a saw, a pole pruner, a clearing saw or a brush cutter, a blower device and/or a leaf blower.

8. The method according to claim 1, wherein
the source of pollution is dust, tree resin and/or pollen, and
the pollution parameter is a dust concentration, an amount of resin and/or a pollen concentration.

9. The method according to claim 1, wherein
the step a) includes: receiving the pollution parameter via a receiver unit.

10. The method according to claim 1, wherein
the step a) includes: obtaining a meteorological parameter and obtaining the pollution parameter as a function of the obtained meteorological parameter.

11. A method for indirectly obtaining a pollution condition of at least one component of a gardening and/or forestry apparatus, the method comprising the steps of:
   a) obtaining at least one pollution parameter which describes at least one source of pollution prevalent during an operation of the gardening and/or forestry apparatus;
   b) indirectly obtaining the pollution condition of the component based on the obtained pollution parameter; and
   c) outputting and/or transmitting information based on the obtained pollution condition, wherein
   the step a) includes: obtaining a material of a workpiece to be treated by the gardening and/or forestry apparatus and obtaining the pollution parameter as a function of the obtained material.

12. The method according to claim 1, wherein
the step a) includes: obtaining a position of the operation of the gardening and/or forestry apparatus and obtaining the pollution parameter as a function of the obtained position, and/or
the step a) includes: obtaining a marking of a workpiece to be treated by the gardening and/or forestry apparatus and obtaining the pollution parameter as a function of the obtained marking.

13. A gardening and/or forestry apparatus system, comprising:
   a pollution parameter determination device configured to obtain at least one pollution parameter which describes at least one source of pollution prevalent during an operation of a gardening and/or forestry apparatus;
   a pollution condition determination device configured to indirectly obtain a pollution condition of at least one component of the gardening and/or forestry apparatus based on the obtained pollution parameter; and
   an output and/or transmission device configured to output and/or to transmit information based on the obtained pollution condition, wherein
   the information includes the obtained pollution condition, and/or
   wherein the gardening and/or forestry apparatus system is configured to obtain a cleaning and/or maintenance reminder for the component based on the obtained pollution condition, wherein the information includes the cleaning and/or maintenance reminder.

14. The gardening and/or forestry apparatus system according to claim 13, further comprising:
   a mobile determination device, which includes the pollution parameter determination device, the pollution condition determination device and/or the output and/or transmission device.

15. The gardening and/or forestry apparatus system according to claim 13, further comprising:
   the gardening and/or forestry apparatus.

* * * * *